(12) United States Patent
Souryal

(10) Patent No.: US 11,771,550 B2
(45) Date of Patent: Oct. 3, 2023

(54) SAFE-RELEASE BONE FASTENER FOR USE WITH A LIGAMENT AUGMENTATION STRAP

(71) Applicant: Tarek O. Souryal, Dallas, TX (US)

(72) Inventor: Tarek O. Souryal, Dallas, TX (US)

( * ) Notice: Subject to any disclaimer, the term of this patent is extended or adjusted under 35 U.S.C. 154(b) by 366 days.

(21) Appl. No.: 17/153,505

(22) Filed: Jan. 20, 2021

(65) Prior Publication Data

US 2021/0220115 A1    Jul. 22, 2021

Related U.S. Application Data

(60) Provisional application No. 62/963,424, filed on Jan. 20, 2020.

(51) Int. Cl.
*A61F 2/08* (2006.01)

(52) U.S. Cl.
CPC ..... *A61F 2/0811* (2013.01); *A61F 2002/0817* (2013.01); *A61F 2002/0852* (2013.01)

(58) Field of Classification Search
CPC ............ A61F 2/0811; A61F 2002/0835; A61F 2002/0852; A61F 2002/0882
See application file for complete search history.

(56) References Cited

U.S. PATENT DOCUMENTS

| 6,042,609 | A | * | 3/2000 | Giordano | A61F 2/0811 |
| | | | | | 424/423 |
| 7,500,983 | B1 | * | 3/2009 | Kaiser | A61B 17/0401 |
| | | | | | 606/232 |
| 9,888,998 | B2 | * | 2/2018 | Sengun | A61F 2/0811 |
| 2007/0049944 | A1 | * | 3/2007 | Stone | A61F 2/0811 |
| | | | | | 606/86 A |
| 2008/0195145 | A1 | * | 8/2008 | Bonutti | A61B 17/683 |
| | | | | | 606/205 |
| 2012/0290004 | A1 | * | 11/2012 | Lombardo | A61B 17/0401 |
| | | | | | 606/232 |
| 2016/0354195 | A1 | * | 12/2016 | Spenciner | A61F 2/08 |
| 2017/0202658 | A1 | * | 7/2017 | Sengun | A61B 17/0401 |

\* cited by examiner

*Primary Examiner* — Matthew J Lawson

(57) ABSTRACT

This disclosure provides an apparatus, system and method for ligament augmentation strap assembly. The ligament augmentation strap assembly includes an ligament augmentation strap inserted through a hole previously drilled through two adjacent bones; and a safe-release bone fastener attached to end of the ligament augmentation strap and configured to collapse when a force greater than a threshold is applied from the ligament augmentation strap.

16 Claims, 4 Drawing Sheets

SAFE-RELEASE BONE FASTENER FOR USE WITH A LIGAMENT AUGMENTATION STRAP

CROSS-REFERENCE TO RELATED APPLICATIONS

This application claims priority to U.S. Provisional Patent Application Ser. No. 62/963,424 entitled SAFE-RELEASE BONE FASTENER FOR USE WITH A LIGAMENT AUGMENTATION STRAP and filed on Jan. 20, 2020. The content of the above-identified patent document is hereby incorporated by reference.

TECHNICAL FIELD

This invention relates in general to surgical devices, more particularly, to an apparatus for a medical suture using a safe release bone fastener.

BACKGROUND

Surgeries occasionally necessitate sutures to be fastened between two bones to help secure a joint. A fastener is generally one option for securing the suture when a single hole is drilled through the bone structures. Depending on the strength of the suture, the bones, and the fastener, damage could be caused to the bones around the joint if excessive force is placed upon the joint.

SUMMARY

This disclosure provides a safe release bone fastener for use with any ligament augmentation strap between two bones and related methods.

In a first embodiment, a ligament augmentation strap (LAA) assembly is provided. The LAA assembly includes a ligament augmentation strap inserted through a hole previously drilled through two adjacent bones; and a safe release bone fastener is attached to end of the LAA and configured to collapse when a force greater than a threshold is applied from the ligament augmentation strap.

In a second embodiment, a safe-release bone fastener for use with a medical thread is provided. The safe-release bone fastener is configured to secure a medical thread threaded through a hole previously drilled through two adjacent bones; and collapse when a force greater than a threshold is applied from the medical thread.

In a third embodiment, a method for using an ligament augmentation strap assembly is provided. The method includes inserting the LAA through a hole previously drilled through two adjacent bones; attaching a safe-release bone fastener to end of the LAA; and collapsing the safe-release bone fastener when a force greater than a threshold is applied from the ligament augmentation strap.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; and the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like. Definitions for certain words and phrases are provided throughout this patent document, those of ordinary skill in the art should understand that in many, if not most instances, such definitions apply to prior as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

FIGS. 1 through 4, discussed below, and the various embodiments used to describe the principles of the present disclosure in this patent document are by way of illustration only and should not be construed in any way to limit the scope of the disclosure.

Figure 1:
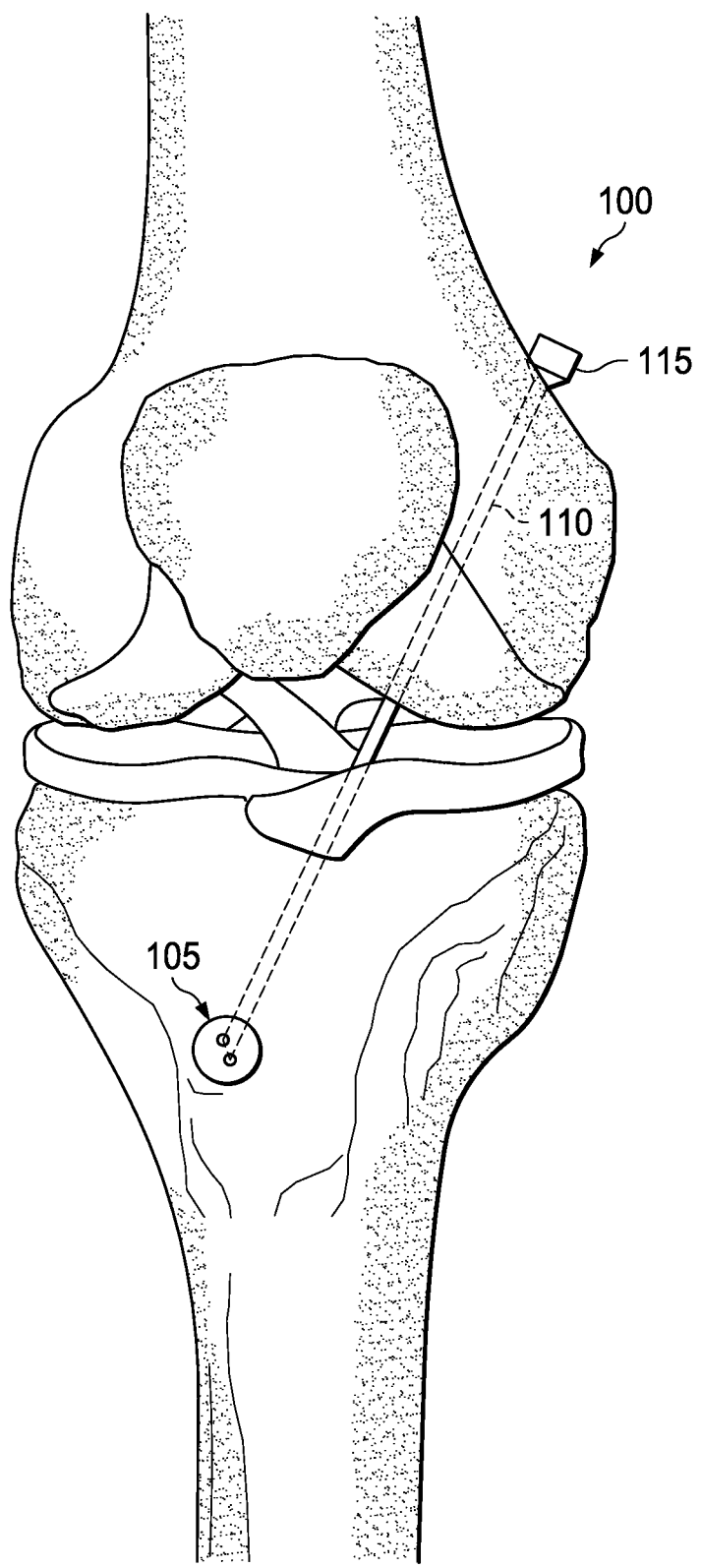
FIG. 1 illustrates an example ligament augmentation strap assembly using a safe-release bone fastener according to this disclosure.

FIG. 1 illustrates an example ligament augmentation strap assembly 100 using a safe-release bone fastener 105 according to this disclosure. The embodiments of the LAA assembly 100 illustrated in FIG. 1 is for illustration only. FIG. 1 does not limit the scope of this disclosure to any particular implementation of a brace assembly.

The brace assembly 100 can be used to hold secure or reinforce a joint between two bones. The brace assembly 100 can include a safe-release bone fastener 105, a ligament augmentation strap 110, and an anchor fastener 115. As illustrated, the brace assembly in FIG. 1 is depicted at a joint between a femur and a tibia, but can be used in any embodiment to secure any two bones.

The safe-release bone fastener 105 is attached at one end of the ligament augmentation strap 110 to secure the LAA from protruding outside of the bone. The safe-release bone fastener 105 can be fitted into a depression cut into the bone in a manner to lie flush with the surface of the bone. More detail regarding the safe-release bone fastener 105 are described in relation to FIGS. 2A-3D.

The ligament augmentation strap 110 is used to secure the two bones where tissue or muscle has been diminished or for any other reason that the two bones need securing. The ligament augmentation strap 110 can be flexible or a pivot for bending when the two bones are rotating in relation to each other.

The anchor fastener 115 is connected to an opposite side of the ligament augmentation strap 110 from the safe-release bone fastener 105. The anchor fastener 115 can be integral to the ligament augmentation strap 110 or can be a separate component. The anchor fastener 115 is used in combination with the safe-release bone fastener 105 to ensure that the placement of the ligament augmentation strap 110 is fixed.

Figure 2A:
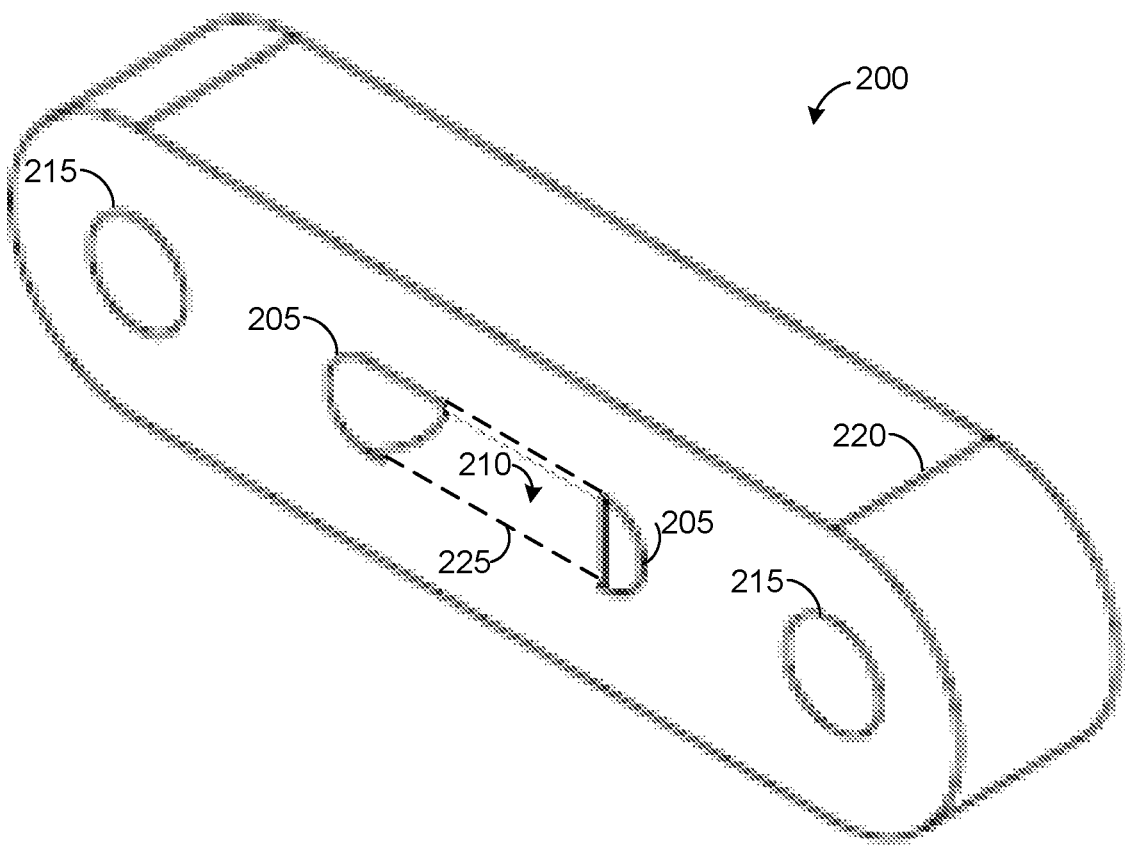
FIGS. 2A and 2B illustrate an example safe-release bone fastener according to this disclosure.
Figure 2B:
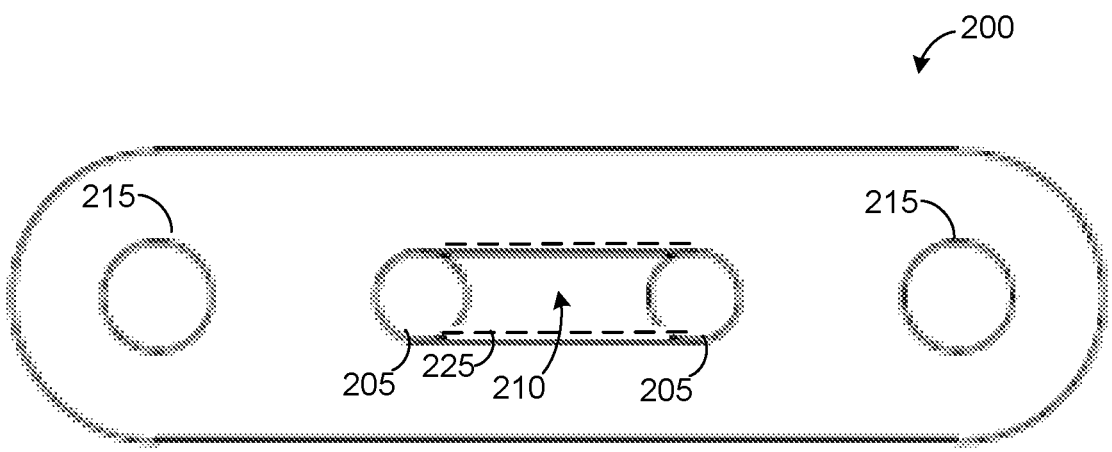

FIGS. 2A and 2B illustrate an example safe-release bone fastener 200 according to this disclosure. FIG. 2A illustrates an isometric view of the safe-release bone fastener 200 according to the various embodiments of the present disclosure. FIG. 2B illustrates a front view of the safe-release bone fastener 200. The embodiments of the safe-release bone fastener 200 illustrated in FIGS. 2A and 2B are for illustration only. FIGS. 2A and 2B do not limit the scope of this disclosure to any particular implementation of a safe-release bone fastener.

The safe-release bone fastener 200 is an example of the safe-release bone fastener 105 illustrated in FIG. 1. The safe-release bone fastener 200 is used for securing any ligament augmentation strap 110 opposite to an anchor fastener 115. The safe-release bone fastener 200 can also be used with surgical sutures. The safe-release bone fastener 200 includes primary holes 205, a bridge 210, and secondary holes 215.

The primary holes 205 are used to connect to the ligament augmentation strap 110. A type of surgical thread can be threaded through one primary hole 205 and through a second primary hole 205.

In certain embodiments, two threads could be used that are attached to the end of the ligament augmentation strap to aid in passage of the construct. One of the threads can be threaded through the first primary hole 205 and the other thread can be threaded through the second primary hole 205. The first and second threads could then be tied together on an opposite side of the safe-release bone fastener 200 from the ligament augmentation strap 110.

The bridge 210 is an area between the primary holes 205 with a reduced thickness from the thickness 220 of the safe-release bone fastener 200. The thickness of the bridge 210 can be determined based on an amount of force a bone can withstand. For example, a typical femur requires around 4,000 Newtons to damage a bone, such as a femur. The thickness of the bridge can be based on an amount of material the bridge is made of breaking below 4,000 Newtons. The thickness can also include a safety factor for other unknown factors or variability of the bone. While the maximum thickness can be determined based on the strength of the bone, the minimum thickness can be based on the practicality of the fastener. For example, the thickness of the bridge 210 can be based on the amount of expected forces on the joint. For example, common joint movements and forces could produce forces of 500 Newtons, for example. The thickness of the bridge 210 would need to be able to at least take forces of the 500 Newtons without collapsing.

The bridge 210 can also be structured with a safety factor on either the minimum thickness or the maximum thickness. While the forces experienced in everyday life could be 500 Newtons, for example, unexpected forces might occur that would be above this force, but below the damaging force. Thus, the bridge 210 could be designed to have a thickness at a factor, such as 20 percent, greater than the minimum thickness or less than the maximum thickness.

The bridge 210 can also be structured with perforations 225 that run between the primary holes 205 for the thickness 220 of the break-away fastener 200 on each side of the bridge 210. The perforations 225 can be designed to fail at the maximum force or minimum force of the bones. The perforations 225 can be in designed in a similar manner as the maximum thickness. The perforations 225 can be used in place or in combination with the designed thickness. Using perforations 225 would also decrease the chance of small portions of the safe-release bone fastener 200 breaking from the bridge 210.

Figure 3A:
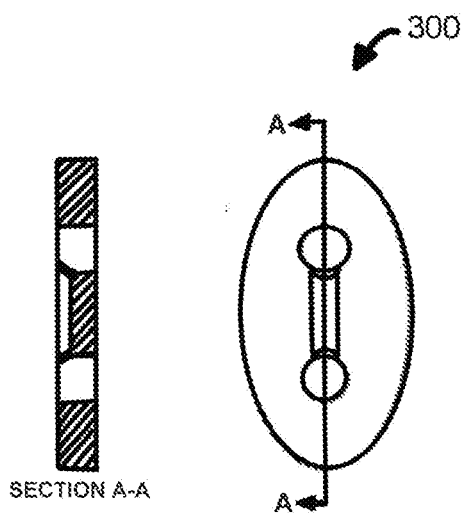
FIGS. 3A-3D illustrate an example pregnant guide pin drill passer according to this disclosure.
Figure 3B:
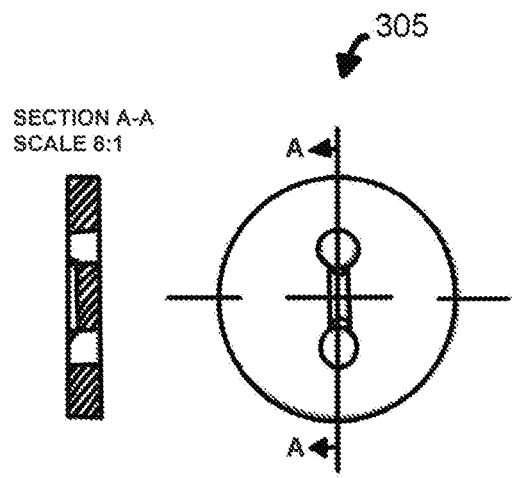
Figure 3C:
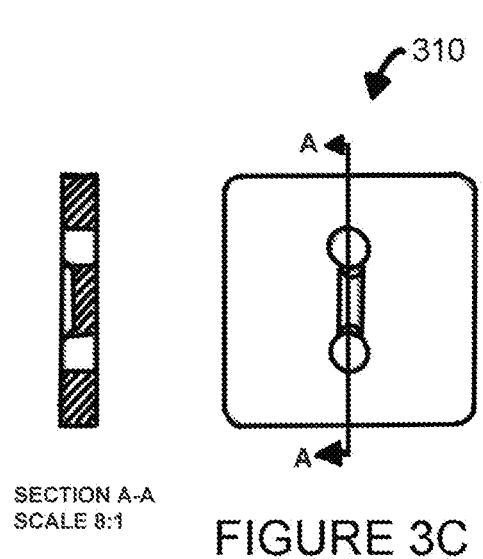
Figure 3D:
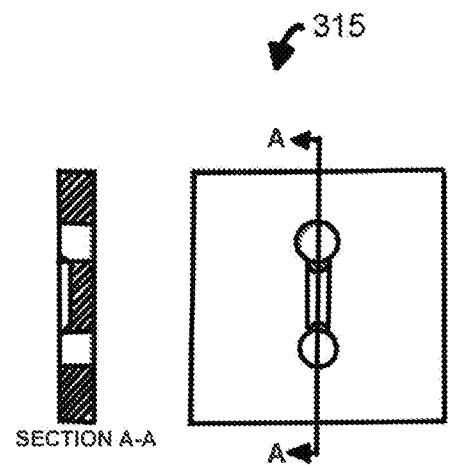

FIGS. 3A-3D illustrate example safe-release bone fastener 105 of different shapes according to this disclosure. FIG. 3A illustrates an oval safe-release bone fastener 300 according to the various embodiments of the present disclosure. FIG. 3B illustrates a circle safe-release bone fastener 305 according to the various embodiments of the present disclosure. FIG. 3C illustrates a rounded square safe-release bone fastener 310 according to the various embodiments of the present disclosure. FIG. 3D illustrates a square safe-release bone fastener 315 according to the various embodiments of the present disclosure. The embodiments of the safe-release bone fastener illustrated in FIGS. 3A-3D are for illustration only. FIGS. 3A-3D do not limit the scope of this disclosure to any particular implementation of a safe-release bone fastener.

Figure 4:
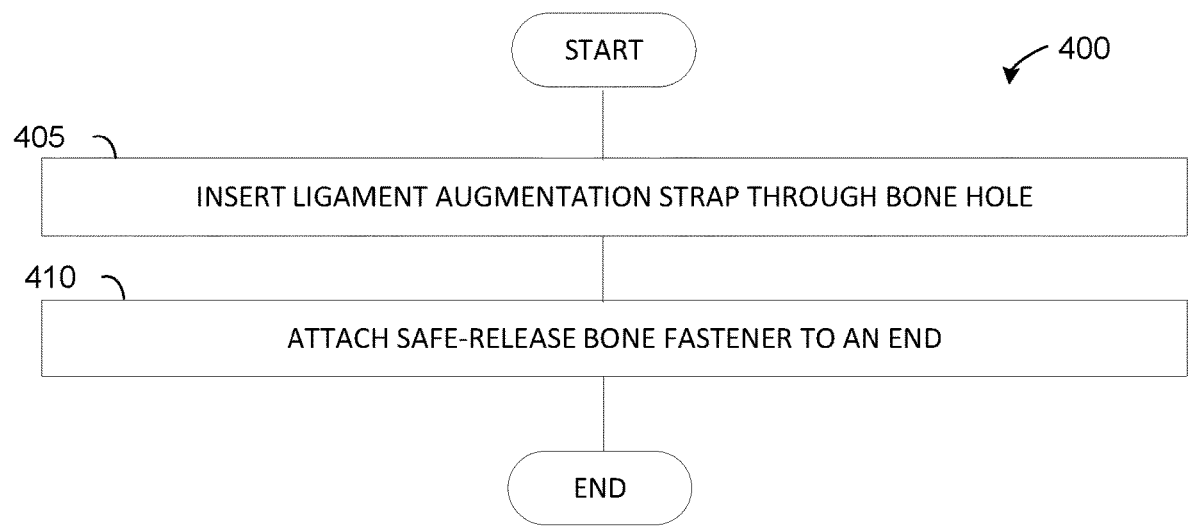
FIG. 4 illustrates an example process of using a ligament augmentation strap assembly with a safe-release bone fastener according to this disclosure.

FIG. 4 illustrates an example process of using a brace assembly 100 with a safe-release bone fastener 105 according to this disclosure. For example, the process depicted in FIG. 4 may be performed by the brace assembly 100 illustrated in FIG. 1.

In operation 405, the ligament augmentation strap 110 is inserted through a hole drilled through two bones for reducing the forces at the joint. The ligament augmentation strap 110 is inserted until the anchor fastener 115 is flush with the bone in which the ligament augmentation strap 110 is first inserted. A portion of the ligament augmentation strap 110 that is flexible or otherwise rotatable is positioned in between the bones.

In operation 410, safe-release bone fastener 105 can be attached at the end of the ligament augmentation strap 110 opposite of the anchor fastener 115. The safe-release bone fastener 105 can have one or more threads pass through the primary holes 205 in order to be secured. The threads will pass over a bridge 210 between the holes that have a reduced thickness from the thickness 220 of the safe-release bone fastener 105. The bridge 210 can have round edges in order for the thread to not rub or break due to the forces applied from the ligament augmentation strap 110.

The bridge 210 can collapse when a force applied from the ligament augmentation strap 110 exceeds a safety threshold. As the ligament augmentation strap receives different forces from the movement of the joint, the bridge 210 can collapse to avoid putting the forces on the bones in a manner that would cause permanent damage to the bones.

Although FIG. 4 illustrates an example of using a safe-release bone fastener for use with a ligament augmentation strap, various changes could be made to FIG. 4. For example, while shown as a series of steps, various steps in each figure could overlap, occur in parallel, occur in a different order, or occur multiple times.

Although the present disclosure has been described with exemplary embodiments, various changes and modifications may be suggested to one skilled in the art. It is intended that the present disclosure encompass such changes and modifications as fall within the scope of the appended claims.

What is claimed is:

1. A ligament augmentation strap assembly comprising:
   a ligament augmentation strap configured to be inserted through a hole previously drilled through two adjacent bones; and
   a safe-release bone fastener configured to be attached to an end of the ligament augmentation strap and including a bridge between two holes in the safe-release bone fastener, the bridge is configured to break-away from a remaining portion of the safe-release bone fastener when a force greater than a threshold is applied from the ligament augmentation strap.

2. The ligament augmentation strap assembly of claim 1, wherein the ligament augmentation strap is configured to be attached through the two holes in the safe-release bone fastener.

3. The ligament augmentation strap assembly of claim 1, wherein the bridge has a thickness that is reduced from a thickness of the safe-release bone fastener outside of the two holes.

4. The ligament augmentation strap assembly of claim 3, wherein the bridge includes perforations on each side that run between the two holes for the thickness of the safe-release bone fastener.

5. The ligament augmentation strap assembly of claim 4, wherein the perforations of the bridge are designed to break at a force greater than a threshold strength based on an amount of force sufficient to cause damage to at least one of the two adjacent bones.

6. The ligament augmentation strap assembly of claim 1, wherein the bridge has less than a threshold strength based on an amount of force sufficient to cause damage to at least one of the two adjacent bones.

7. A safe-release bone fastener for use with a medical thread, the safe-release bone fastener configured to:
   secure the medical thread threaded through a hole previously drilled through two adjacent bones,
   wherein the safe-release bone fastener includes a bridge between two holes in the safe-release bone fastener, the bridge is configured to break-away from a remaining portion of the safe-release bone fastener when a force greater than a threshold is applied from the medical thread.

8. The safe-release bone fastener of claim 7, wherein the bridge has a thickness that is reduced from a thickness of the safe-release bone fastener outside of the two holes.

9. The safe-release bone fastener of claim 8, wherein the bridge includes perforations on each side that run between the two holes for the thickness of the safe-release bone fastener.

10. The safe-release bone fastener of claim 9, wherein the perforations of the bridge are designed to break at a force greater than a threshold strength based on an amount of force sufficient to cause damage to at least one of the two adjacent bones.

11. The safe-release bone fastener of claim 7, wherein the bridge has less than a threshold strength based on an amount of force sufficient to cause damage to at least one of the two adjacent bones.

12. A method for use of a ligament augmentation strap assembly, the method comprising:
   inserting the ligament augmentation strap through a hole previously drilled through two adjacent bones;
   attaching a safe-release bone fastener to an end of the ligament augmentation strap; and
   breaking away a bridge between two holes in the safe-release bone fastener from a remaining portion of the safe-release bone fastener when a force greater than a threshold is applied from the ligament augmentation strap.

13. The method of claim 12, wherein the ligament augmentation strap is attached through the two holes in the safe-release bone fastener.

14. The method of claim 12, wherein the bridge has a thickness that is reduced from the thickness of the safe-release bone fastener outside of the two holes.

15. The method of claim 14, wherein:
   the bridge includes perforations on each side that run between the two holes for the thickness of the safe-release bone fastener; and
   the perforations of the bridge are designed to break at a force greater than a threshold strength based on an amount of force sufficient to cause damage to at least one of the two adjacent bones.

16. The method of claim 12, wherein the bridge has less than a threshold strength based on an amount of force sufficient to cause damage to at least one of the two adjacent bones.

* * * * *